(12) United States Patent
Patel et al.

(10) Patent No.: US 10,179,800 B2
(45) Date of Patent: Jan. 15, 2019

(54) CRYSTALLINE FORMS OF S-[4-(3-FLUORO-3-METHYLBUTYRYLOXY) BUT-2-YNYL]6-α,9-α-DIFLUORO-17-α-(FURAN-2-YL)CARBONYLOXY-11-β-HYDROXY-16-α-METHYL-3-OXOANDROSTA-1,4-DIENE-17-β-CARBOTHIOATE

(71) Applicant: Sun Pharma Advanced Research Company Limited, Andheri (e) Mumbai (IN)

(72) Inventors: Jiten Ranchhodbhai Patel, Baroda (IN); Gopalkumar Chimanlal Patel, Baroda (IN); Gaurav Sanjivkumar Sheth, Baroda (IN); Trinadha Rao Chitturi, Baroda (IN)

(73) Assignee: Sun Pharma Advanced Research Company Limited, Andheri (e) Mumbai (IN)

( * ) Notice: Subject to any disclaimer, the term of this patent is extended or adjusted under 35 U.S.C. 154(b) by 0 days.

(21) Appl. No.: 15/547,748

(22) PCT Filed: Jan. 30, 2016

(86) PCT No.: PCT/IN2016/050034
§ 371 (c)(1),
(2) Date: Jul. 31, 2017

(87) PCT Pub. No.: WO2016/120894
PCT Pub. Date: Aug. 4, 2016

(65) Prior Publication Data
US 2018/0016297 A1    Jan. 18, 2018

(30) Foreign Application Priority Data
Jan. 31, 2015  (IN) .......................... 323/MUM/2015

(51) Int. Cl.
*C07J 31/00*    (2006.01)

(52) U.S. Cl.
CPC ......... *C07J 31/006* (2013.01); *C07B 2200/13* (2013.01)

(58) Field of Classification Search
CPC .......................... C07J 31/006; C07B 2200/13
See application file for complete search history.

(56) References Cited

FOREIGN PATENT DOCUMENTS

| WO | WO-2014192027 A1 | 12/2014 |
| WO | WO-2016120894 A1 | 8/2016 |

OTHER PUBLICATIONS

Bhattacharya et al., Polymorphism in Pharmaceutical Solids: Thermoanalytical and Crystallographic Methods 3374 (Brittain H. ed., 2d ed. Informa Healthcare USA, Inc. 2009) (1999) (Year: 1999).*
Ivanisevic, I., Pharm. Form. Qual. 30-33, 32 (2011) (Year: 2011).*
"International Application Serial No. PCT/IN2016/050034, International Search Report dated May 31, 2016", 3 pgs.
"International Application Serial No. PCT/IN2016/050034, Written Opinion dated May 31, 2016", 4 pgs.

* cited by examiner

*Primary Examiner* — Timothy R Rozof
(74) *Attorney, Agent, or Firm* — Schwegman Lundberg & Woessner, P.A.

(57) ABSTRACT

The present invention relates to crystalline forms of S-[4-(3-fluoro-3-methylbutyryloxy)but-2-ynyl] 6α,9α-difluoro-17α-(furan-2-yl)carbonyloxy-11β-hydroxy-16α-methyl-3-oxoandrosta-1,4-diene-17β-carbothioate, an anti-inflammatory and anti-allergic glucocorticoid compound.

9 Claims, 8 Drawing Sheets

CRYSTALLINE FORMS OF S-[4-(3-FLUORO-3-METHYLBUTYRYLOXY) BUT2-YNYL]6-α,9-α-DIFLUORO-17-α-(FURAN-2-YL)CARBONYLOXY-11-β-HYDROXY-16-α-METHYL-3-OXOANDROSTA-1,4-DIENE-17-β-CARBOTHIOATE

PRIORITY APPLICATIONS

This application is a U.S. national stage application filed under 35 U.S.C. § 371 from International Application Serial No. PCT/IN2016/050034, which was filed 30 Jan. 2016, and published as WO 2016/120894 on 4 Aug. 2016, and which claims priority to India Application No. 323/MUM/2015, filed 31 Jan. 2015, which applications and publication are incorporated by reference as if reproduced herein and made a part hereof in their entirety, and the benefit of priority of each of which is claimed herein.

FIELD OF THE INVENTION

The present invention relates to crystalline forms of S-[4-(3-fluoro-3-methylbutyryloxy)but-2-ynyl]6α,9α-difluoro-17α-(furan-2-yl)carbonyloxy-11β-hydroxy-16α-methyl-3-oxoandrosta-1,4-diene-17β-carbothioate, an anti-inflammatory and anti-allergic glucocorticoid compound.

BACKGROUND OF THE INVENTION

Glucocorticosteroids having anti-inflammatory properties are widely used for the treatment of inflammatory conditions or disorders of skin, airways, eye, GI tract, joints, CNS etc, and several autoimmune disorders. Some of the inflammatory skin disorders where treatment with glucocorticoids is prescribed are eczema, psoriasis, allergic dermatitis, pruritis, hypersensitivity reactions etc. Inflammatory or allergic conditions of the airways for which glucocorticoids are used include disorders of nose, throat or lungs such as rhinitis (including hay fever), nasal polyps, asthma (including allergen-induced asthmatic reaction), chronic obstructive pulmonary disease (COPD), interstitial lung disease, fibrosis, etc. Glucocorticoid administration is also used for inflammatory bowel disorders such as ulcerative colitis and Crohn's diseases; and inflammatory joint disorders such as rheumatoid arthritis which are autoimmune diseases.

However, administration of corticosteroids in general may cause, in addition to the desired pharmacological effect, undesirable or adverse side effects at sites distant from the target tissue, the so-called systemic effects. Some of the undesired systemic effects encountered include widespread immunosuppression, increased bone turnover, impaired growth, skin thinning, diabetes, obesity, water retention, progesterone and estrogen related disorders. It is therefore desirable to have glucocorticoids which possess potent anti-inflammatory activity at the target tissue, with minimal or preferably no systemic activity at therapeutic doses when used for chronic treatment.

Our interest to develop compounds which act at the specific site of inflammation with insignificant or no noteworthy side effects has led us to the discovery of novel, safe 11β-hydroxyandrosta-4-ene-3-one compounds described in U.S. Pat. No. 8,785,425 and PCT application WO2014192027. These compounds possess useful anti-inflammatory activity whilst having insignificant or no noteworthy systemic side effects at multiples of efficacious dose. WO 2014192027 specifically discloses a compound of Formula I Formula I which substantially meets the desired attributes, i.e. good anti-inflammatory effects at the target tissue whilst having insignificant or no noteworthy systemic side effects at multiples of efficacious dose. The processes disclosed in application WO2014192027 involve isolation of the compound of Formula I from a mixture of methanol and dichloromethane eluted during purification by column chromatography. The white solid obtained therein was found to be amorphous in nature. The amorphous form was found to be unstable upon storage even at ambient conditions. It is crucial to have a polymorphic form which is stable, which can be produced consistently and is suitable for the preparation of stable formulations. Thus, there is a need to develop new polymorphic form/s of the compound of Formula I which is/are stable, consistent and reproducible.

SUMMARY OF THE INVENTION

Present invention provides crystalline S-[4-(3-fluoro-3-methylbutyryloxy)but-2-ynyl]6α,9α-difluoro-17α-(furan-2-yl)carbonyloxy-11β-hydroxy-16α-methyl-3-oxoandrosta-1,4-diene-17β-carbothioate of Formula I.

Formula I

In one aspect of the present invention there is provided crystalline Form 1 of the compound S-[4-(3-fluoro-3-methylbutyryloxy)but-2-ynyl]6α,9α-difluoro-17α-(furan-2-yl)carbonyloxy-11β-hydroxy-16α-methyl-3-oxoandrosta-1,4-diene-17β-carbothioate characterized by X-ray powder diffraction peaks (XRPD) at 15.7, 19.3, 24.1 and 29.9 (±0.1) degree 2θ. The Form 1 is further characterized by a differential scanning calorimetry (DSC) thermogram with an endotherm at 141.5° C. (±2.0° C.) and a melting endotherm at 180.0° C. (±2.0° C.).

In another aspect of the present invention there is provided crystalline Form 2 of the compound S-[4-(3-fluoro-3-methylbutyryloxy)but-2-ynyl]6α,9α-difluoro-17α-(furan-2-yl)carbonyloxy-11β-hydroxy-16α-methyl-3-oxoandrosta-1,4-diene-17β-carbothioate of Formula I characterized by X-ray powder diffraction peaks at 15.2, 18.5, 19.7, 23.7 and 27.3 (±0.1) degree 2θ. The Form 2 is further characterized by a differential scanning calorimetry thermogram with an endoderm at 145.5° C. (±0.5° C.) and a melting endotherm at 179.0° C. (±2.0° C.).

In another aspect of the present invention there is provided crystalline Form 3 of the compound S-[4-(3-fluoro-3-methylbutyryloxy)but-2-ynyl]6α,9α-difluoro-17α-(furan-2-yl)carbonyloxy-11β-hydroxy-16α-methyl-3-oxoandrosta-1,4-diene-17β-carbothioate of Formula I characterized by X-ray powder diffraction peaks at 6.0, 8.3, 14.0 and 16.8 (±0.1) degree 2θ. The Form 3 is further characterized by a differential scanning calorimetry thermogram with an endotherm at 187.9° C. (±1.0° C.).

DETAILED DESCRIPTION OF THE INVENTION

According to one aspect of the present invention, there is provided compound S-[4-(3-fluoro-3-methylbutyryloxy)but-2-ynyl]6α,9α-difluoro-17α-(furan-2-yl)carbonyloxy-11β-hydroxy-16α-methyl-3-oxoandrosta-1,4-diene-17β-carbothioate of Formula I Formula I in crystalline form.

In one embodiment the crystalline form is a white solid.

Figure 1:
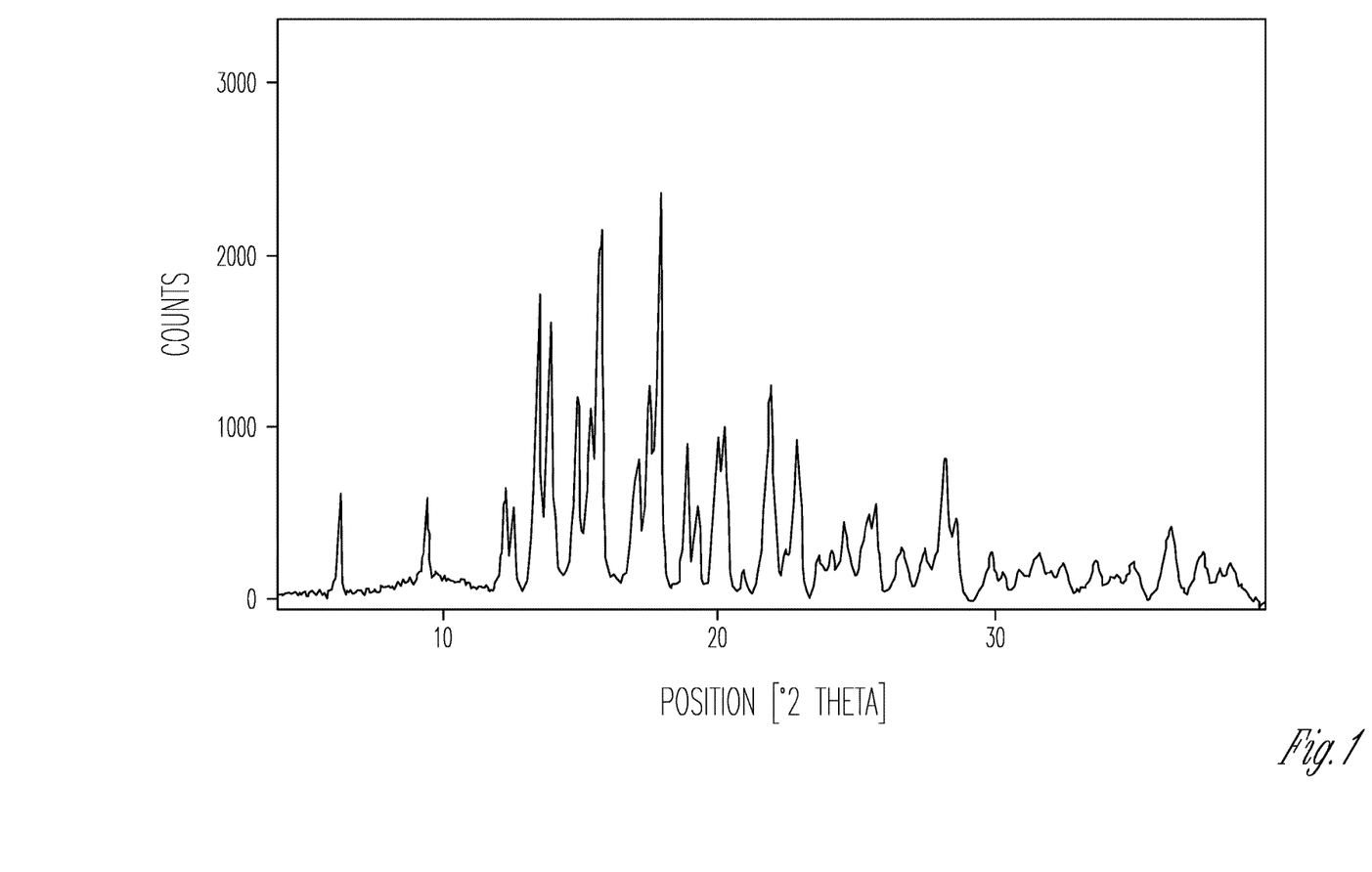
FIG. 1: XRPD profile of compound of Formula I polymorphic Form 1.

As an embodiment of the invention, there is provided crystalline Form 1 of a compound S-[4-(3-fluoro-3-methylbutyryloxy)but-2-ynyl]6α,9α-difluoro-17α-(furan-2-yl)carbonyloxy-11β-hydroxy-16α-methyl-3-oxoandrosta-1,4-diene-17β-carbothioate of Formula I characterized by X-ray powder diffraction peaks at 15.7, 19.3, 24.1 and 29.9 (±0.1) degree 2θ. The Form 1 is further characterized by X-ray diffraction peaks at 12.3, 14.9, 17.0, 24.7, 25.8, 28.3, 28.7, 31.7, 35.1 and 36.5 (±0.1) degree 2θ. The XRPD pattern for Form 1 is provided in FIG. 1.

Figure 2:
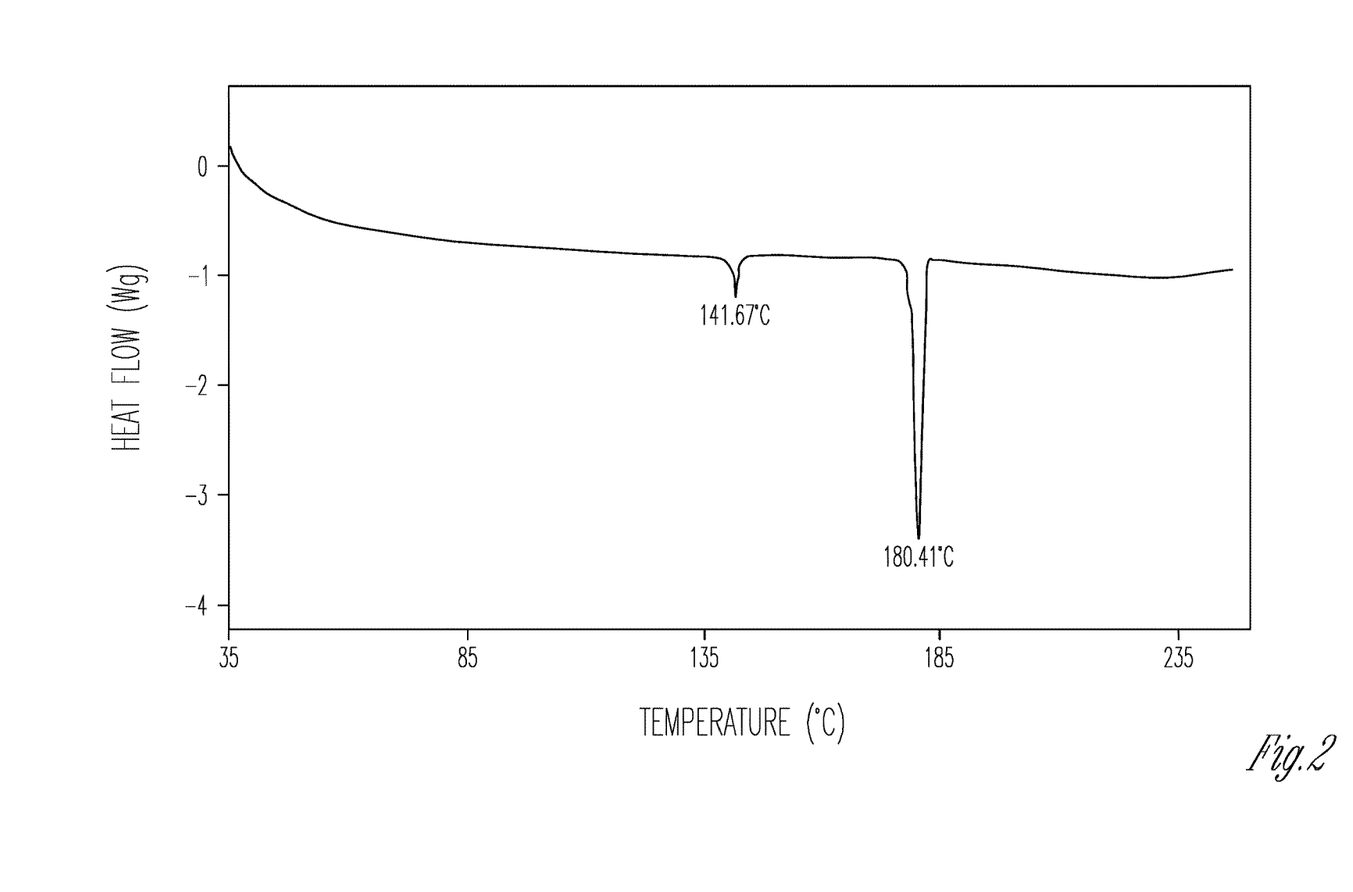
FIG. 2: DSC profile of compound of Formula I polymorphic Form 1.

In another embodiment the present invention provides Form 1 of compound of Formula I characterized by a DSC thermogram with an endotherm at 141.0° C. (±2.0° C.) and a melting endotherm at 180.0° C. (±2.0° C.). The DSC thermogram for Form 1 is provided in the FIG. 2.

The crystalline Form 1 can be prepared by crystallizing the compound of Formula I from a suitable solvent. Suitable solvent for the purpose may be selected from ketones like acetone and methylethyl ketone, or $C_1$-$C_4$ alcohols like isobutyl alcohol, methanol, ethanol, t-butanol, n-butanol; esters like ethyl acetate; ethers like tetrahydrofuran and 1,4-dioxane; hydrocarbons like toluene; dimethylacetamide, dimethylformamide or halogenated solvents like dichloromethane. Preferred solvent is acetone.

In one embodiment the solvent for preparing Form 1 is acetone.

Crystallization may be facilitated by methods such as cooling, partial removal of the solvent from the mixture, seeding, adding an anti-solvent to the solution, or any combination thereof.

In one embodiment the method of crystallization comprises a cooling step.

The mixture may be cooled to temperatures below 20° C. to further facilitate the crystallization process.

In one embodiment the method of crystallization comprises a step which results in partial removal of solvent.

In one embodiment the method of crystallization comprises a seeding step.

In one embodiment the method of crystallization comprises addition of an anti-solvent to the solution.

Anti-solvent is a liquid miscible with the solvent which reduces solute solubility. The selection of the suitable anti-solvent is under the purview of a person skilled in the art. Anti-solvent suitable for the purpose may include water, cyclohexane, heptane, diisopropyl ether etc.

Crystalline Form 1 may be isolated form the mixture thereof by techniques well known in the art.

Figure 3:
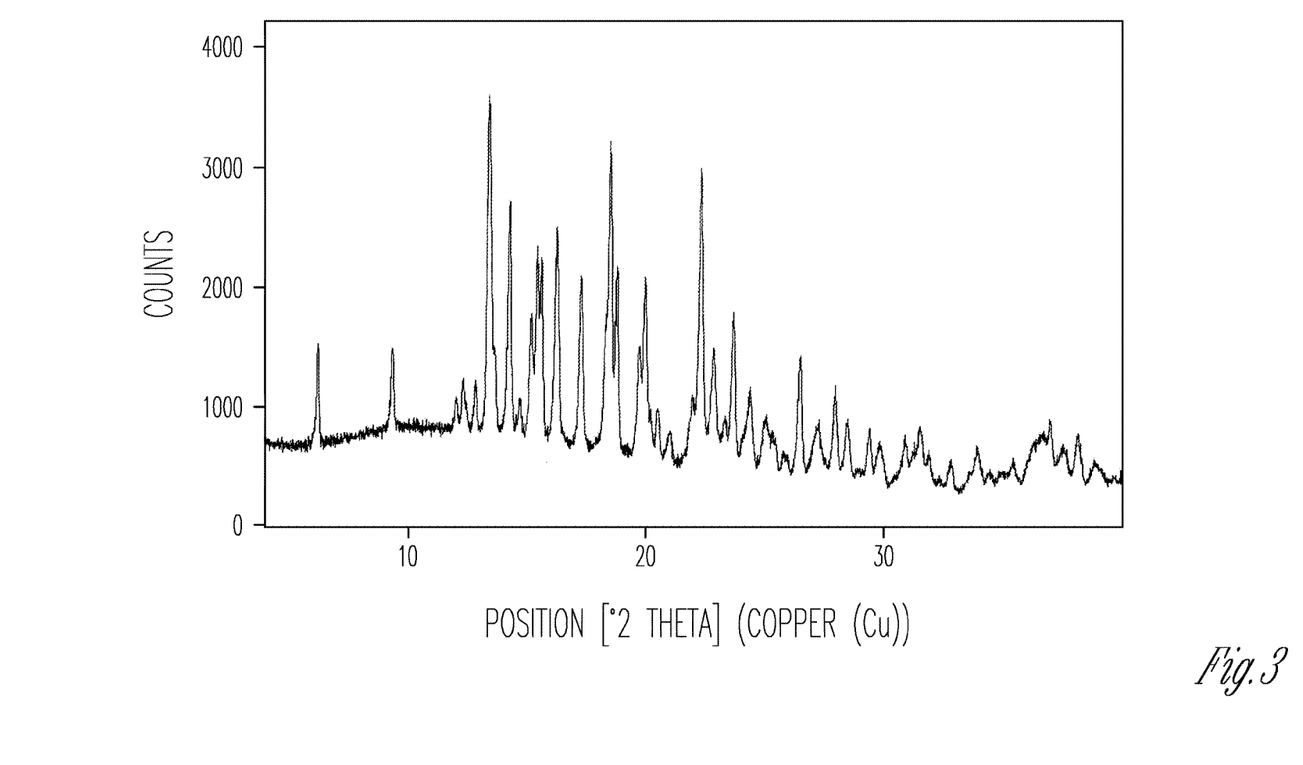
FIG. 3: XRPD profile of compound of Formula I polymorphic Form 2.

In another embodiment, there is provided crystalline Form 2 of the compound S-[4-(3-fluoro-3-methylbutyryloxy)but-2-ynyl]6α,9α-difluoro-17α-(furan-2-yl)carbonyloxy-11β-hydroxy-16α-methyl-3-oxoandrosta-1,4-diene-17β-carbothioate of Formula I characterized by X-ray powder diffraction peaks at 15.2, 18.5, 19.7, 23.7 and 27.3 (±0.1) degree 2θ. The Form 2 can be further characterized by X-ray powder diffraction peaks at 13.4, 14.3, 16.3, 17.3, 20.0, 22.3, 26.5 and 28.0 (±0.1) degree 2θ. The XRPD pattern for Form 2 is provided in FIG. 3.

Figure 4:
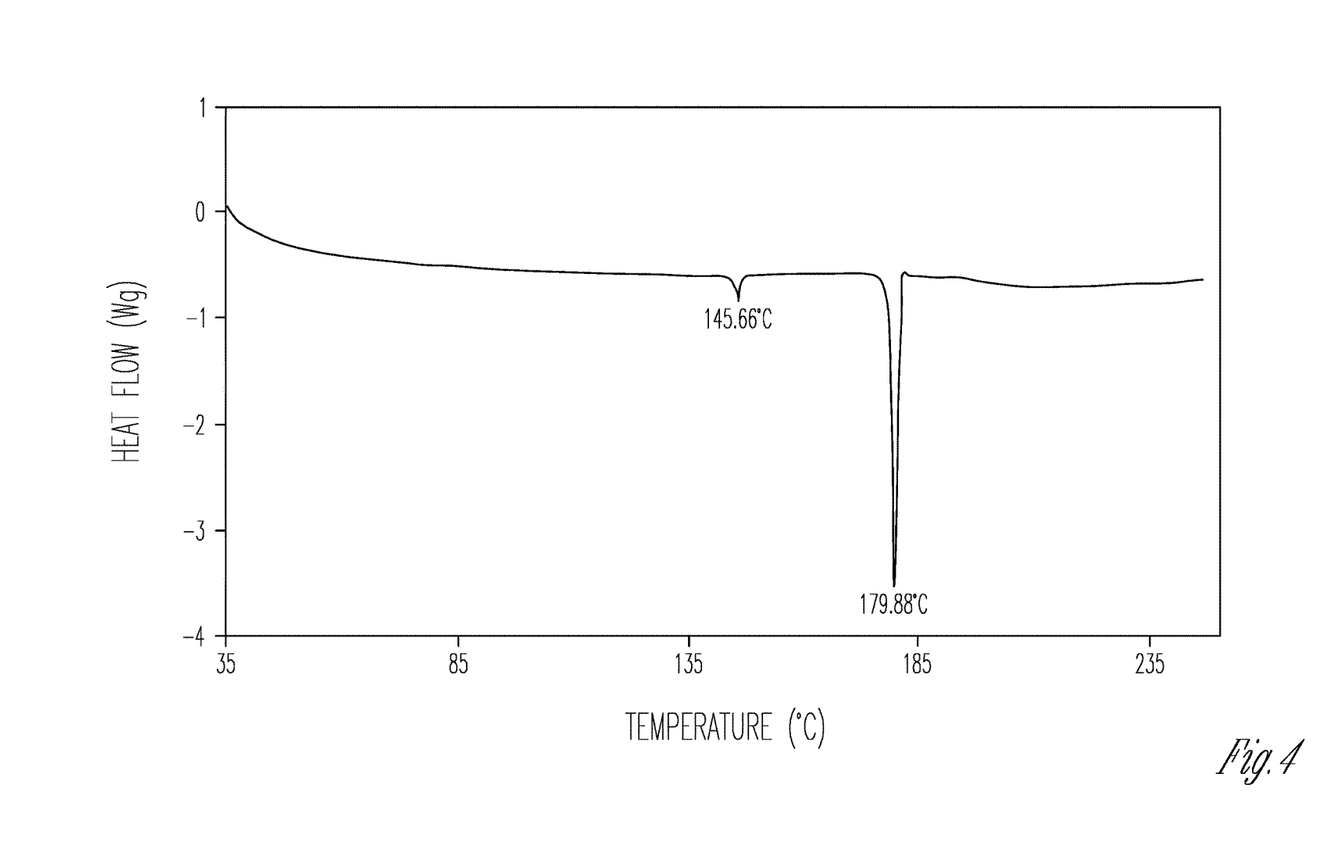
FIG. 4: DSC profile of compound of Formula I polymorphic Form 2.
Figure 5:
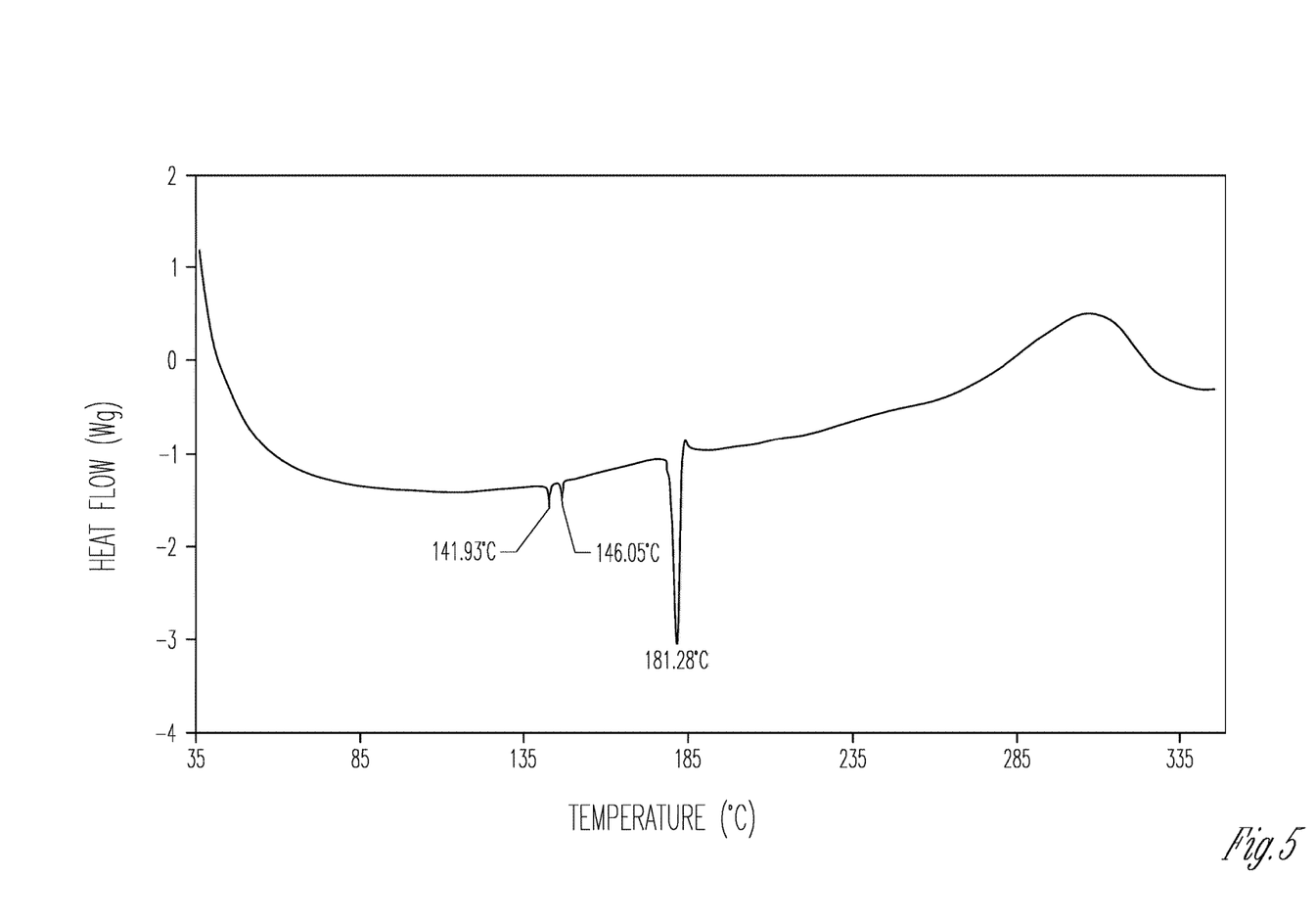
FIG. 5: DSC profile of 1:1 mixture of Form 1 and Form 2.

In another embodiment the present invention provides Form 2 of compound of Formula I characterized by a DSC thermogram with endotherm at 145.5° C. (±0.5° C.) and a melting endotherm at 179.0° C. (±2.0° C.). The DSC thermogram for Form 2 is provided in the FIG. 4. FIG. 5 provides DSC profile of 1:1 mixture of From 1 and Form 2.

The crystalline Form 2 may be prepared by forming a solution of compound of Formula I in a solvent by heating at a temperature from about 50° C. to the reflux temperature, optionally seeding the solution with crystals of Form 2, and gradually cooling the solution to between 10° C. to 30° C. with stirring (10-50 rpm). Cooling may be performed at a rate of about 10-25° C./hour. Crystalline Form 2 may be isolated form the mixture thereof by techniques well known in the art. A suitable solvent for preparing the crystalline Form 2 may be selected from $C_1$-$C_4$ alcohols, preferably isopropanol.

In one embodiment the solvent for preparing Form 2 is isopropanol.

Figure 6:
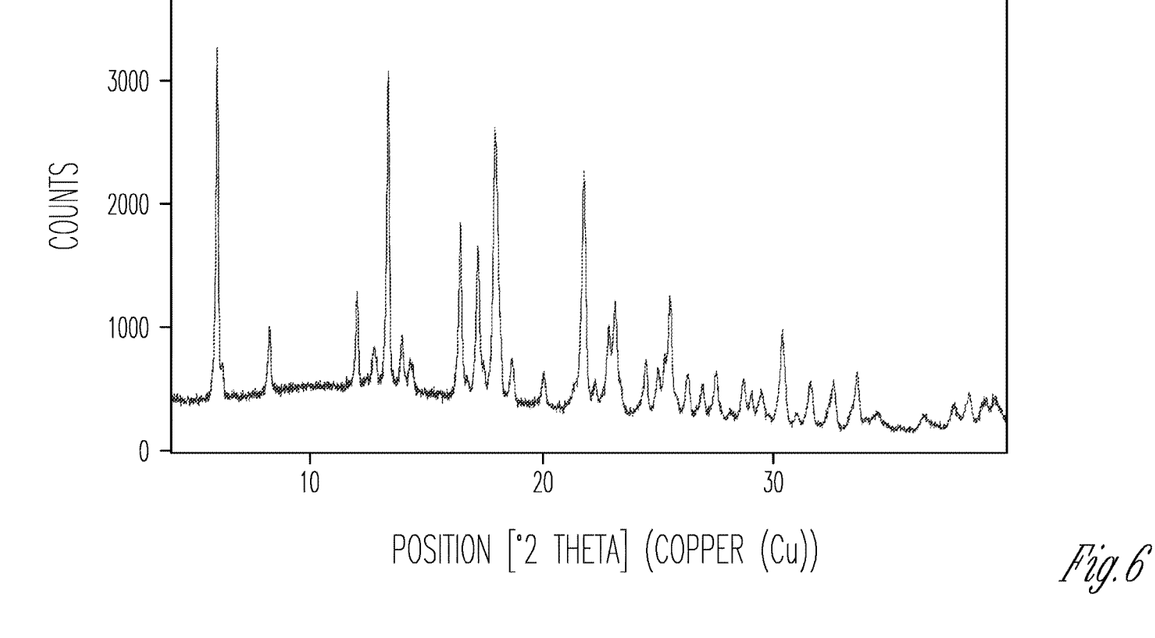
FIG. 6: XRPD profile of compound of Formula I polymorphic Form 3.

In another embodiment, there is provided crystalline Form 3 of the compound S-[4-(3-fluoro-3-methylbutyryloxy)but-2-ynyl]6α,9α-difluoro-17α-(furan-2-yl)carbonyloxy-11β-hydroxy-16α-methyl-3-oxoandrosta-1,4-diene-17β-carbothioate of Formula I characterized by X-ray powder diffraction peaks at 6.0, 8.3, 14.0 and 16.8 (±0.1) degree 2θ. The Form 3 can be further characterized by X-ray diffraction peaks at 12.0, 13.3, 16.4, 17.2, 17.9, 21.75, 22.8, 23.1, 25.5 and 30.3 (±0.1) degree 2θ. The XRPD pattern for Form 3 is provided in FIG. 6.

Figure 7:
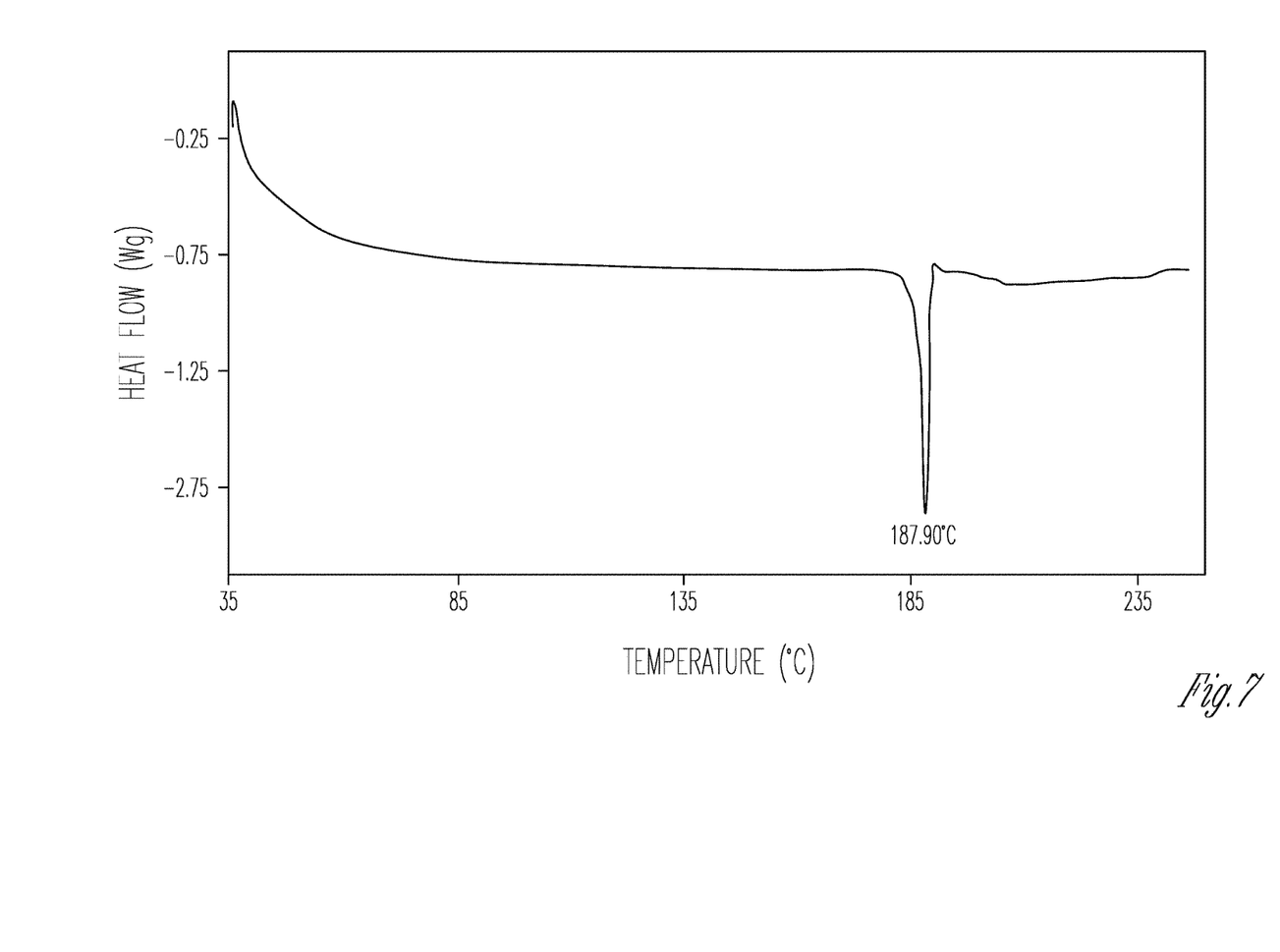
FIG. 7: DSC profile of compound of Formula I polymorphic Form 3.

In another embodiment the present invention provides Form 3 of compound of Formula I characterized by a DSC thermogram with an endotherm at 187.9° C. (±1.0° C.). The DSC thermogram for Form 3 is provided in the FIG. 7.

The crystalline Form 3 may be prepared by stirring a mixture of crystalline Form 2 and water for more than 7 days or by heating the mixture at about 90° C. to about 95° C. with stirring for about 12 to 24 hours. Crystalline Form 3 may be isolated from the mixture thereof by the methods well known in the art.

Another embodiment of the current invention is the preparation of amorphous form of compound of Formula I, which comprises freeze drying a clear solution of compound of Formula I from a suitable solvent. Alternatively, amorphous form of compound of Formula I is prepared by spray drying or flash drying from its clear solution in a suitable solvent.

Figure 8:
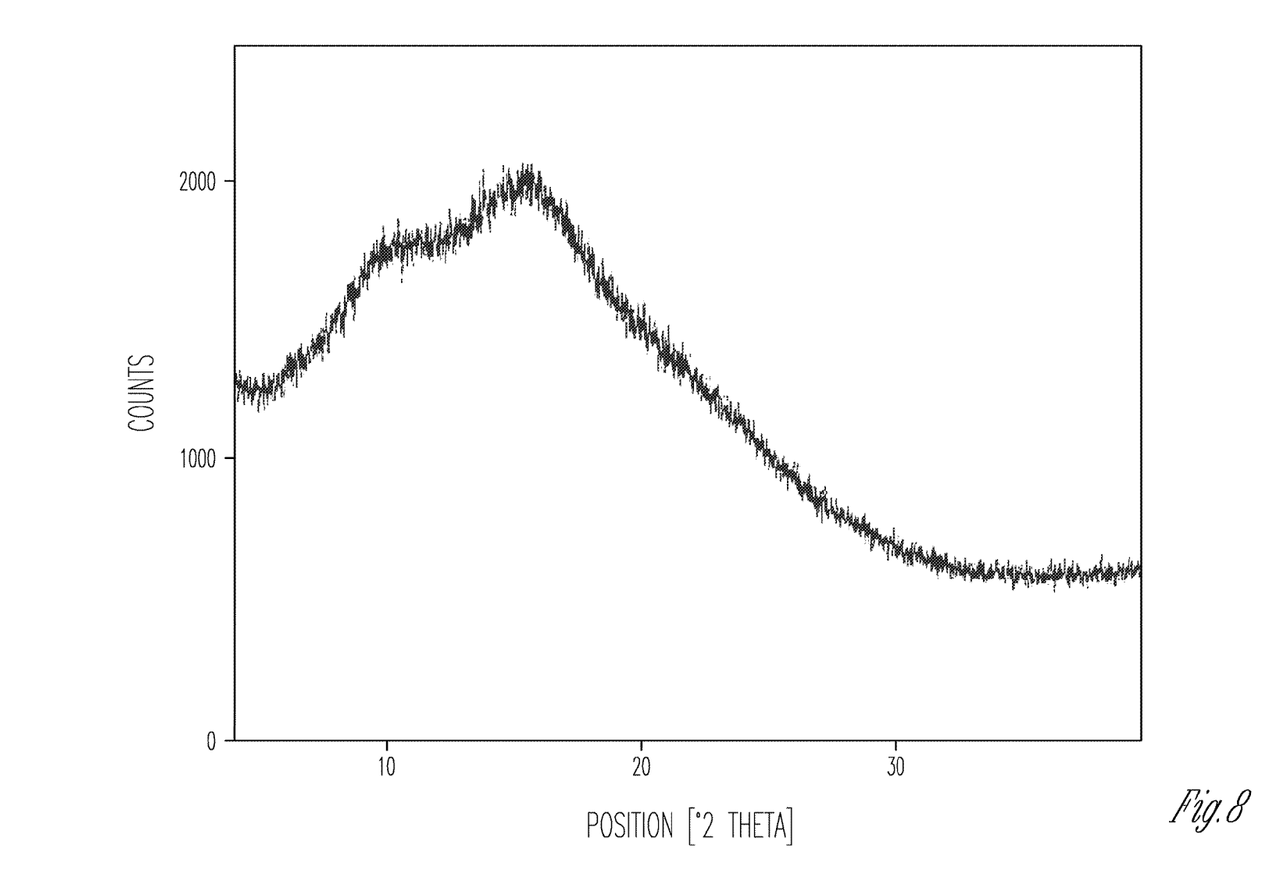
FIG. 8: XRPD profile of compound of Formula I amorphous Form.

In another embodiment, the present invention provides a process for the preparation of amorphous S-[4-(3-fluoro-3-methylbutyryloxy)but-2-ynyl]-6α,9α-difluoro-17α-(furan-2-yl) carbonyloxy-11β-hydroxy-16α-methyl-3-oxoandrosta-1,4-diene-17β-carbothioate by freeze drying a solution of compound of Formula I in a solvent which may selected from a $C_2$-$C_4$ alcohol, or mixtures thereof, or their mixture with water. Preferably the solvent for freeze drying is t-butanol. The amorphous form did not show any peaks in X-ray powder diffraction as shown in FIG. 8.

Technical references such as patents and applications are incorporated herein by reference. Any embodiments specifically and explicitly recited herein may form the basis of a disclaimer either alone or in combination with one or more further embodiments.

The following non-limiting Examples illustrate the invention:

EXAMPLES

Powder x-ray diffraction patterns were obtained by methods known in the art using PANalytical Model EMPYREAN. Tube conditions were 40 mA 45 kV CuKα. 2-theta range was 4° to 40°.

Measurements of difference between the temperature of a sample and a reference pan that were subject to the same temperature program (differential scanning calorimetry, DSC) were obtained on a TA Instruments model DSC Q2000Differential Scanning calorimeter with temperature programming 35° C. to 250° C. at the ramp rate of 10° C./min.

Example-1: S-[4-(3-fluoro-3-methylbutyryloxy)but-2-ynyl]-6α,9α-difluoro-17α-(furan-2-yl) carbonyloxy-11β-hydroxy-16α-methyl-3-oxoandrosta-1,4-diene-17β-carbothioate (Crystalline Form 1)

To a clear solution of S-[4-(3-fluoro-3-methylbutyryloxy)but-2-ynyl] 6α,9α-difluoro-17α-(furan-2-yl)carbonyloxy-11β-hydroxy-16α-methyl-3-oxoandrosta-1,4-diene-17β-carbothioate (15.6 g) in acetone (62 ml) at 28-30° C. was added slowly DM water (~150 ml) during 40-45 min. The mixture was cooled to 18-20° C. and stirred for 1 h. The crystallized product was filtered, washed with DM water, and dried at 60-65° C. under vacuum to yield the title compound as white solid as polymorphic Form 1.

Example-2: S-[4-(3-fluoro-3-methylbutyryloxy)but-2-ynyl]6α,9α-difluoro-17α-(furan-2-yl)carbonyloxy-11β-hydroxy-16α-methyl-3-oxoandrosta-1,4-diene-17β-carbothioate (Crystalline Form 2)

S-[4-(3-fluoro-3-methylbutyryloxy)but-2-ynyl]6α,9α-difluoro-17α-(furan-2-yl)carbonyloxy-11β-hydroxy-16α-methyl-3-oxoandrosta-1,4-diene-17β-carbothioate (25.8 g) was dissolved under stirring in isopropanol (232 ml) at 75-80° C. The solution is then cooled gradually to 28-30° C. during 3 h under slow stirring. The recrystallized product was filtered, washed with chilled isopropanol and dried at 60-65° C. under vacuum to yield white solid of the title compound as crystalline Form 2.

Example-3: S-[4-(3-fluoro-3-methylbutyryloxy)but-2-ynyl]6α,9α-difluoro-17α-(furan-2-yl)carbonyloxy-11β-hydroxy-16α-methyl-3-oxoandrosta-1,4-diene-17β-carbothioate (Crystalline Form 2)

S-[4-(3-fluoro-3-methylbutyryloxy)but-2-ynyl]6α,9α-difluoro-17α-(furan-2-yl)carbonyloxy-11β-hydroxy-16α-methyl-3-oxoandrosta-1,4-diene-17β-carbothioate (14.4 g) was dissolved under stirring in isopropanol (130 ml) at 75-80° C. Cool this solution slowly to 64-66° C. and seed the clear solution with Form 2 (86 mg) and cool it slowly to 28-30° C. within 30 min. The crystallized product was filtered, washed with chilled isopropanol, and dried at 60-65° C. under vacuum to yield the title compound as white solid.

Example-4: S-[4-(3-fluoro-3-methylbutyryloxy)but-2-ynyl]6α,9α-difluoro-17α-(furan-2-yl)carbonyloxy-11β-hydroxy-16α-methyl-3-oxoandrosta-1,4-diene-17β-carbothioate (Crystalline Form 3)

Mixture of 0.5 g of Form 2 in 20 ml water was stirred at 90-95° C. for 1 h and kept at 90-95° C. for 24 h. The fine needle shaped crystals were filtered, washed with water and dried at 65° C. under vacuum to yield crystalline Form 3 of the title compound as white solid.

Example-5: S-[4-(3-fluoro-3-methylbutyryloxy)but-2-ynyl]6α,9α-difluoro-17α-(furan-2-yl)carbonyloxy-11β-hydroxy-16α-methyl-3-oxoandrosta-1,4-diene-17β-carbothioate (Amorphous Form)

A solution of S-[4-(3-fluoro-3-methylbutyryloxy)but-2-ynyl]6α,9α-difluoro-17α-(furan-2-yl)carbonyloxy-11β-hydroxy-16α-methyl-3-oxoandrosta-1,4-diene-17β-carbothioate (2.0 g) in t-butanol (100 ml) freeze dried under vacuum for 12 h. The resulting powder was further dried at 60-65° C. under vacuum to remove traces of solvent to yield title compound as a white amorphous powder.

We claim:

1. A compound S-[4-(3-fluoro-3-methylbutyryloxy)but-2-ynyl]6α,9α-difluoro-17α-(furan-2-yl)carbonyloxy-11β-hydroxy-16α-methyl-3-oxoandrosta-1,4-diene-17β-carbothioate of Formula I Formula I in crystalline form;
wherein the crystalline form is Form 1 and is characterized by X-ray powder diffraction peaks at 15.7, 19.3, 24.1 and 29.9 (±0.1) degree 2θ.

2. The crystalline Form 1 of claim 1, which is further characterized by X-ray diffraction peaks at 12.3, 14.9, 17.0, 24.7, 25.8, 28.3, 28.7, 31.7, 35.1 and 36.5 (±0.1) degree 2θ.

3. A crystalline Form 1 of claim 1 further characterized by a differential scanning calorimetry thermogram with an endoderm at 141.0° C. (±2.0° C.) and a melting endotherm at 180.0° C. (±2° C.).

4. A compound S-[4-(3-fluoro-3-methylbutyryloxy)but-2-ynyl]6α,9α-difluoro-17α-(furan-2-yl)carbonyloxy-11β-hydroxy-16α-methyl-3-oxoandrosta-1,4-diene-17β-carbothioate of Formula I Formula I wherein the crystalline form is Form 2 and is characterized by X-ray powder diffraction peaks at 15.2, 18.5, 19.7, 23.7 and 27.3 (±0.1) degree 2θ.

5. The crystalline Form 2 of claim 4, which is further characterized by X-ray diffraction peaks at 13.4, 14.3, 16.3, 17.3, 20.0, 22.3, 26.5 and 28.0 (±0.1) degree 2θ.

6. The crystalline Form 2 of claim 4 further characterized by a differential scanning calorimetry thermogram with an endoderm at 145.5° C. (±0.5° C.) and a melting endotherm at 179.0 (±2.0° C.).

7. A compound S-[4-(3-fluoro-3-methylbutyryloxy)but-2-ynyl]6α,9α-difluoro-17α-(furan-2-yl)carbonyloxy-11β-hydroxy-16α-methyl-3-oxoandrosta-1,4-diene-17β-carbothioate of Formula I Formula I wherein the crystalline form is Form 3 and is characterized by X-ray powder diffraction peaks at 6.0, 8.3, 14.0 and 16.8 (±0.1) degree 2θ.

8. The crystalline Form 3 of claim 7, which is further characterized by X-ray diffraction peaks at 12.0, 13.3, 16.4, 17.2, 17.9, 21.75, 22.8, 23.1, 25.5 and 30.3 (±0.1) degree 2θ.

9. The crystalline Form 3 of claim 7 further characterized by a differential scanning calorimetry thermogram with an endoderm at 187.9° C. (±1.0° C.).

* * * * *